US008975577B2

(12) United States Patent
Geromanos et al.

(10) Patent No.: US 8,975,577 B2
(45) Date of Patent: Mar. 10, 2015

(54) SYSTEM AND METHOD FOR GROUPING PRECURSOR AND FRAGMENT IONS USING SELECTED ION CHROMATOGRAMS

(71) Applicant: Waters Technologies Corporation, Milford, MA (US)

(72) Inventors: Scott J. Geromanos, Middletown, NJ (US); Jeffrey Cruz Silva, Beverly, MA (US); Guo-Zhong Li, Westborough, MA (US); Marc Victor Gorenstein, Needham, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 14/454,828

(22) Filed: Aug. 8, 2014

(65) Prior Publication Data

US 2015/0028199 A1  Jan. 29, 2015

Related U.S. Application Data

(63) Continuation of application No. 13/859,964, filed on Apr. 10, 2013, now Pat. No. 8,835,837, which is a continuation of application No. 12/806,937, filed on Aug. 24, 2010, now Pat. No. 8,436,298, which is a continuation of application No. 11/596,584, filed as application No. PCT/US2005/017743 on May 20, 2005, now Pat. No. 7,800,055.

(60) Provisional application No. 60/572,503, filed on May 20, 2004.

(51) Int. Cl.
*B01D 59/44* (2006.01)
*H01J 49/00* (2006.01)
*G01N 30/72* (2006.01)
*H01J 49/26* (2006.01)
*G01N 33/68* (2006.01)

(52) U.S. Cl.
CPC .......... *G01N 30/7233* (2013.01); *H01J 49/005* (2013.01); *H01J 49/26* (2013.01); *H01J 49/0031* (2013.01); *G01N 33/6848* (2013.01)
USPC .......... 250/282; 250/281; 250/283; 250/286; 250/287; 250/288; 702/32; 702/23.36; 210/656; 210/198.2

(58) Field of Classification Search
USPC ......... 250/281–283, 286–288; 702/32, 23.36; 210/656, 198.2
See application file for complete search history.

(56) References Cited

U.S. PATENT DOCUMENTS

| | | | | |
|---|---|---|---|---|
| 6,717,130 B2* | 4/2004 | Bateman et al. | ............... | 250/282 |
| 6,982,414 B2* | 1/2006 | Bateman et al. | ............... | 250/282 |
| 7,645,984 B2* | 1/2010 | Gorenstein et al. | ........... | 250/281 |
| 7,800,055 B2* | 9/2010 | Geromanos et al. | ........... | 250/288 |
| 7,851,742 B2* | 12/2010 | Geromanos et al. | .......... | 250/282 |
| 8,017,908 B2* | 9/2011 | Gorenstein et al. | ........... | 250/282 |
| 8,436,298 B2* | 5/2013 | Geromanos et al. | .......... | 250/282 |
| 8,835,837 B2* | 9/2014 | Geromanos et al. | .......... | 250/282 |

\* cited by examiner

*Primary Examiner* — David Porta
*Assistant Examiner* — Meenakshi Sahu
(74) *Attorney, Agent, or Firm* — Muirhead and Saturnelli, LLC

(57) ABSTRACT

LC/MS data generated by an LC/MS system is analyzed to determine groupings of ions associated with originating molecules. Ions are grouped initially according to retention time, for example, using retention time or chromatographic peaks in mass chromatograms. After initial groupings are determined based on retention time, ion peak shapes are compared to determine whether ions should be excluded. Ions having peak shapes not matching other ions, or alternatively a reference peak shape, are excluded from the group.

23 Claims, 17 Drawing Sheets

| Mass Component | Retention Time (Scan Number or Minutes) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 1 | 0 | 0 | 0 | 1 | 1 | 1 | 1 | 1 | 0 | 2 | 2 | 2 | 2 | 0 | 0 |
| 2 | 0 | 3 | 3 | 3 | 3 | 3 | 0 | 0 | 0 | 0 | 4 | 4 | 4 | 4 | 0 |
| 3 | 0 | 0 | 5 | 5 | 5 | 5 | 5 | 0 | 0 | 0 | 6 | 6 | 6 | 0 | 0 |
| 4 | 0 | 0 | 0 | 0 | 7 | 7 | 7 | 7 | 7 | 0 | 0 | 0 | 0 | 0 | 0 |
| 5 | 0 | 8 | 8 | 8 | 8 | 0 | 0 | 0 | 0 | 9 | 9 | 9 | 9 | 0 | 0 |
| 6 | 0 | 10 | 10 | 10 | 10 | 0 | 0 | 0 | 0 | 0 | 11 | 11 | 11 | 0 | 0 |
| 7 | 0 | 0 | 0 | 0 | 12 | 12 | 12 | 12 | 12 | 0 | 13 | 13 | 13 | 0 | 0 |
| 8 | 0 | 14 | 14 | 14 | 14 | 14 | 0 | 0 | 0 | 0 | 15 | 15 | 15 | 15 | 0 |
| 9 | 0 | 16 | 16 | 16 | 16 | 0 | 0 | 0 | 0 | 17 | 17 | 17 | 17 | 0 | 0 |
| 10 | 0 | 0 | 0 | 0 | 18 | 18 | 18 | 18 | 18 | 0 | 19 | 19 | 19 | 0 | 0 |
| 11 | 0 | 20 | 20 | 20 | 20 | 20 | 0 | 0 | 0 | 0 | 21 | 21 | 21 | 21 | 0 |
| 12 | 0 | 22 | 22 | 22 | 22 | 0 | 0 | 0 | 0 | 23 | 23 | 23 | 23 | 0 | 0 |
| 13 | 0 | 0 | 0 | 24 | 24 | 24 | 24 | 24 | 0 | 25 | 25 | 25 | 25 | 0 | 0 |
| 14 | 0 | 0 | 0 | 26 | 26 | 26 | 26 | 26 | 0 | 27 | 27 | 27 | 27 | 0 | 0 |
| 15 | 0 | 0 | 0 | 28 | 28 | 28 | 28 | 28 | 0 | 0 | 29 | 29 | 29 | 0 | 0 |

Figure 3

| | Retention Time (Scan Number or Minutes) | | | | | | | | | | | | | | |
|---|---|---|---|---|---|---|---|---|---|---|---|---|---|---|---|
| 1  | 0 | 0  | 0   | 6   | 17  | 100 | 17 | 6  | 0  | 20 | 100 | 40  | 20  | 0  | 0 |
| 2  | 0 | 6  | 25  | 100 | 25  | 6   | 0  | 0  | 0  | 0  | 13  | 25  | 100 | 13 | 0 |
| 3  | 0 | 0  | 2   | 10  | 100 | 30  | 6  | 0  | 0  | 0  | 10  | 100 | 7   | 0  | 0 |
| 4  | 0 | 0  | 0   | 0   | 9   | 100 | 34 | 17 | 11 | 0  | 0   | 0   | 0   | 0  | 0 |
| 5  | 0 | 25 | 100 | 25  | 8   | 0   | 0  | 0  | 0  | 20 | 100 | 40  | 20  | 0  | 0 |
| 6  | 0 | 25 | 100 | 25  | 8   | 0   | 0  | 0  | 0  | 0  | 10  | 100 | 7   | 0  | 0 |
| 7  | 0 | 0  | 0   | 0   | 9   | 100 | 34 | 17 | 11 | 0  | 10  | 100 | 7   | 0  | 0 |
| 8  | 0 | 6  | 25  | 100 | 25  | 6   | 0  | 0  | 0  | 0  | 13  | 25  | 100 | 13 | 0 |
| 9  | 0 | 25 | 100 | 25  | 8   | 0   | 0  | 0  | 0  | 20 | 100 | 40  | 20  | 0  | 0 |
| 10 | 0 | 0  | 0   | 0   | 9   | 100 | 34 | 17 | 11 | 0  | 10  | 100 | 7   | 0  | 0 |
| 11 | 0 | 6  | 25  | 100 | 25  | 6   | 0  | 0  | 0  | 0  | 13  | 25  | 100 | 13 | 0 |
| 12 | 0 | 25 | 100 | 25  | 8   | 0   | 0  | 0  | 0  | 20 | 100 | 40  | 20  | 0  | 0 |
| 13 | 0 | 0  | 0   | 6   | 17  | 100 | 17 | 6  | 0  | 20 | 100 | 40  | 20  | 0  | 0 |
| 14 | 0 | 0  | 0   | 6   | 17  | 100 | 17 | 6  | 0  | 20 | 100 | 40  | 20  | 0  | 0 |
| 15 | 0 | 0  | 0   | 6   | 17  | 100 | 17 | 6  | 0  | 0  | 10  | 100 | 7   | 0  | 0 |

400

| Mass-Rt Component | Retention Time (Scan Number or Minutes) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 1 (1) | 0.0 | 0.0 | 0.0 | 5.6 | 16.7 | 100.0 | 16.7 | 5.6 | 0.0 | 0.0 | 0.0 | 0.0 | 0.0 | 0.0 | 0.0 |
| 2 (1) | 0.0 | 0.0 | 0.0 | 0.0 | 0.0 | 0.0 | 0.0 | 0.0 | 0.0 | 20.0 | 100.0 | 40.0 | 20.0 | 0.0 | 0.0 |
| 3 (2) | 0.0 | 6.3 | 25.0 | 100.0 | 25.0 | 6.3 | 0.0 | 0.0 | 0.0 | 0.0 | 0.0 | 0.0 | 0.0 | 0.0 | 0.0 |
| 4 (2) | 0.0 | 0.0 | 0.0 | 0.0 | 0.0 | 0.0 | 0.0 | 0.0 | 0.0 | 0.0 | 12.5 | 25.0 | 100.0 | 12.5 | 0.0 |
| 5 (3) | 0.0 | 0.0 | 2.0 | 10.0 | 100.0 | 30.0 | 6.0 | 0.0 | 0.0 | 0.0 | 0.0 | 0.0 | 0.0 | 0.0 | 0.0 |
| 6 (3) | 0.0 | 0.0 | 0.0 | 0.0 | 0.0 | 0.0 | 0.0 | 0.0 | 0.0 | 0.0 | 10.0 | 100.0 | 6.7 | 0.0 | 0.0 |
| 7 (4) | 0.0 | 0.0 | 0.0 | 0.0 | 8.6 | 100.0 | 34.3 | 17.1 | 11.4 | 0.0 | 0.0 | 0.0 | 0.0 | 0.0 | 0.0 |
| 8 (5) | 0.0 | 25.0 | 100.0 | 25.0 | 8.3 | 0.0 | 0.0 | 0.0 | 0.0 | 0.0 | 0.0 | 0.0 | 0.0 | 0.0 | 0.0 |
| 9 (5) | 0.0 | 0.0 | 0.0 | 0.0 | 0.0 | 0.0 | 0.0 | 0.0 | 0.0 | 20.0 | 100.0 | 40.0 | 20.0 | 0.0 | 0.0 |
| 10 (6) | 0.0 | 25.0 | 100.0 | 25.0 | 8.3 | 0.0 | 0.0 | 0.0 | 0.0 | 0.0 | 0.0 | 0.0 | 0.0 | 0.0 | 0.0 |
| 11 (6) | 0.0 | 0.0 | 0.0 | 0.0 | 0.0 | 0.0 | 0.0 | 0.0 | 0.0 | 0.0 | 10.0 | 100.0 | 6.7 | 0.0 | 0.0 |
| 12 (7) | 0.0 | 0.0 | 0.0 | 0.0 | 8.6 | 100.0 | 34.3 | 17.1 | 11.4 | 0.0 | 0.0 | 0.0 | 0.0 | 0.0 | 0.0 |
| 13 (7) | 0.0 | 0.0 | 0.0 | 0.0 | 0.0 | 0.0 | 0.0 | 0.0 | 0.0 | 0.0 | 10.0 | 100.0 | 6.7 | 0.0 | 0.0 |
| 14 (8) | 0.0 | 6.3 | 25.0 | 100.0 | 25.0 | 6.3 | 0.0 | 0.0 | 0.0 | 0.0 | 0.0 | 0.0 | 0.0 | 0.0 | 0.0 |
| 15 (8) | 0.0 | 0.0 | 0.0 | 0.0 | 0.0 | 0.0 | 0.0 | 0.0 | 0.0 | 0.0 | 12.5 | 25.0 | 100.0 | 12.5 | 0.0 |
| 16 (9) | 0.0 | 25.0 | 100.0 | 25.0 | 8.3 | 0.0 | 0.0 | 0.0 | 0.0 | 0.0 | 0.0 | 0.0 | 0.0 | 0.0 | 0.0 |
| 17 (9) | 0.0 | 0.0 | 0.0 | 0.0 | 0.0 | 0.0 | 0.0 | 0.0 | 0.0 | 20.0 | 100.0 | 40.0 | 20.0 | 0.0 | 0.0 |
| 18 (10) | 0.0 | 0.0 | 0.0 | 0.0 | 8.6 | 100.0 | 34.3 | 17.1 | 11.4 | 0.0 | 0.0 | 0.0 | 0.0 | 0.0 | 0.0 |
| 19 (10) | 0.0 | 0.0 | 0.0 | 0.0 | 0.0 | 0.0 | 0.0 | 0.0 | 0.0 | 0.0 | 10.0 | 100.0 | 6.7 | 0.0 | 0.0 |
| 20 (11) | 0.0 | 6.3 | 25.0 | 100.0 | 25.0 | 6.3 | 0.0 | 0.0 | 0.0 | 0.0 | 0.0 | 0.0 | 0.0 | 0.0 | 0.0 |
| 21 (11) | 0.0 | 0.0 | 0.0 | 0.0 | 0.0 | 0.0 | 0.0 | 0.0 | 0.0 | 0.0 | 12.5 | 25.0 | 100.0 | 12.5 | 0.0 |
| 22 (12) | 0.0 | 25.0 | 100.0 | 25.0 | 8.3 | 0.0 | 0.0 | 0.0 | 0.0 | 0.0 | 0.0 | 0.0 | 0.0 | 0.0 | 0.0 |
| 23 (12) | 0.0 | 0.0 | 0.0 | 0.0 | 0.0 | 0.0 | 0.0 | 0.0 | 0.0 | 20.0 | 100.0 | 40.0 | 20.0 | 0.0 | 0.0 |
| 24 (13) | 0.0 | 0.0 | 0.0 | 5.6 | 16.7 | 100.0 | 16.7 | 5.6 | 0.0 | 0.0 | 0.0 | 0.0 | 0.0 | 0.0 | 0.0 |
| 25 (13) | 0.0 | 0.0 | 0.0 | 0.0 | 0.0 | 0.0 | 0.0 | 0.0 | 0.0 | 20.0 | 100.0 | 40.0 | 20.0 | 0.0 | 0.0 |
| 26 (14) | 0.0 | 0.0 | 0.0 | 5.6 | 16.7 | 100.0 | 16.7 | 5.6 | 0.0 | 0.0 | 0.0 | 0.0 | 0.0 | 0.0 | 0.0 |
| 27 (14) | 0.0 | 0.0 | 0.0 | 0.0 | 0.0 | 0.0 | 0.0 | 0.0 | 0.0 | 20.0 | 100.0 | 40.0 | 20.0 | 0.0 | 0.0 |
| 28 (15) | 0.0 | 0.0 | 0.0 | 5.6 | 16.7 | 100.0 | 16.7 | 5.6 | 0.0 | 0.0 | 0.0 | 0.0 | 0.0 | 0.0 | 0.0 |
| 29 (15) | 0.0 | 0.0 | 0.0 | 0.0 | 0.0 | 0.0 | 0.0 | 0.0 | 0.0 | 0.0 | 10.0 | 100.0 | 6.7 | 0.0 | 0.0 |

| Mass | 600 | 602 | 604 | 606 | 608 | 610 | 612 | 614 | 616 | 618 | 620 | Sequence | Fragment |
|---|---|---|---|---|---|---|---|---|---|---|---|---|---|
| 361.2020 | 16 | 10 | 13 | 19 | 34 | 78 | 100 | 86 | 65 | 37 | 20 | | y"3 |
| 529.3280 | 3 | 2 | 4 | 4 | 35 | 76 | 100 | 90 | 61 | 37 | 18 | A | y"5 |
| 600.3070 | 4 | 5 | 3 | 10 | 45 | 96 | 100 | 93 | 58 | 37 | 25 | T | y"6 |
| 701.3950 | 3 | 3 | 2 | 4 | 34 | 78 | 100 | 94 | 62 | 39 | 20 | E | y"7 |
| 830.3950 | 5 | 3 | 6 | 9 | 35 | 81 | 100 | 96 | 66 | 46 | 24 | S | y"8 |
| 917.4510 | 2 | 2 | 2 | 7 | 40 | 81 | 100 | 91 | 60 | 38 | 20 | F | y"9 |
| 1064.6960 | 2 | 1 | 2 | 3 | 32 | 79 | 100 | 96 | 62 | 39 | 20 | E | y"10 |
| 1175.5740 | 4 | 7 | 8 | 14 | 38 | 81 | 100 | 98 | 66 | 44 | 31 | | y"11-H2O |
| 1193.5930 | 3 | 3 | 5 | 14 | 41 | 74 | 100 | 97 | 81 | 68 | 61 | T | y"11 |
| 1294.6810 | 3 | 2 | 5 | 5 | 36 | 88 | 100 | 88 | 68 | 38 | 25 | | y"12 |

>ECOLI PROTEIN 1789294 PHOSPHOGLYCERATE KINASE, PEPTIDE SEQUENCE: VATEFSETAPATLK

| | Val | Ala | Thr | Glu | Phe | Ser | Glu | Thr | Ala | Pro | Ala | Thr | Leu | Lys |
|---|---|---|---|---|---|---|---|---|---|---|---|---|---|---|
| | 14 | 13 | 12 | 11 | 10 | 9 | 8 | 7 | 6 | 5 | 4 | 3 | 2 | 1 |
| y″ | | 1365.69 | 1294.65 | 1193.61 | 1064.56 | 917.49 | 830.46 | 701.42 | 600.37 | 529.34 | 432.28 | 361.25 | 260.20 | 147.11 |
| y″-H$_2$O | | | | 1179.59 | | | | | | | | | | |

SYSTEM AND METHOD FOR GROUPING PRECURSOR AND FRAGMENT IONS USING SELECTED ION CHROMATOGRAMS

This application is a continuation of U.S. application Ser. No. 13/859,964, filed Apr. 10, 2013, which is a continuation of U.S. application Ser. No. 12/806,937, filed Aug. 24, 2010 (U.S. Pat. No. 8,436,298), which is a continuation of U.S. application Ser. No. 11/596,584, filed Apr. 11, 2008 (U.S. Pat. No. 7,800,055), which is the National Stage of International Application No. PCT/US2005/017743, filed May 20, 2005, which claims priority to U.S. Provisional Application No. 60/572,503 filed May 20, 2004, all of which are hereby incorporated by reference.

RELATED APPLICATIONS

The present application is related to PCT application no. PCT/US2005/017742, entitled "Method and Apparatus for Identifying Proteins in Mixtures,".

BACKGROUND

1. Field of the Invention

The present invention relates generally to proteomics and to the analysis of peptides and proteins in simple and complex mixtures. More specifically, the present invention relates to using liquid chromatography in combination with mass spectrometry to produce peptide precursor ions and fragment ions and to group these peptide precursor ions and fragment ions using selected ion chromatograms.

2. Background of the Invention

Proteomics generally refers to studies involving simple and complex mixtures of proteins. Proteomic studies typically focus on identification or cataloging of proteins in biological systems, or determination of changes in relative abundance among different conditions in biological systems, or both. Identification and quantification of proteins in biological samples is a fundamental problem in proteomics.

Identification and quantification of proteins is crucial to understanding and combating disease, to discovering disease biomarkers, to studying metabolic pathways, and to identifying protein targets in drug discovery. A vital tool in proteomic studies, used to identify and to quantify proteins, is liquid chromatography combined with electrospray ionization mass spectrometry (ESI-LC/MS).

In conventional proteomic studies, proteins of interest typically are first digested to produce a specific set of proteolytic peptides rather than studying the intact proteins directly. The resulting peptides are then characterized during the proteomic analysis. A common proteolytic enzyme used for such digestion is trypsin. In tryptic digestion, the proteins present in the complex mixture are cleaved to produce peptides as determined by the trypsin's cleavage specificity. The trypsin enzyme cleaves proteins along the C-terminal side of the amino acids lysine and arginine.

In LC/MS analysis, the peptide digest is separated and analyzed by liquid chromatographic (LC) separation followed by on-line mass spectrometric (MS) analysis. In the LC separation, the interaction of a peptide with the stationary and mobile phases determines the retention time and chromatographic peak shape of that peptide. We use the term originating molecule to refer to the neutral molecule that is separated by the LC. In the case of tryptic digests, the originating molecules are peptides. The output eluent of the LC, containing the separated, originating molecules is passed to the mass spectrometer.

The ionization source in the mass spectrometer ionizes the originating molecules. The ions corresponding to the originating molecules are called precursors. Once introduced into the mass spectrometer, the precursors can be collisionally dissociated or fragmented into fragment ions. It is the precursor ions and the fragment ions from the originating molecules that are analyzed or mass-measured by the mass spectrometer.

A common method for identifying peptides in a mixture is to compare the mass-analyzed ions to a database containing groups of ions corresponding to known peptides. To make the comparison, the mass analyzed ions must be grouped together into groups of related ions. That is, fragment ions are grouped together into groups likely coming from the same precursor ion.

Conventional techniques make such ions grouping using a tandem mass spectrometer and data dependent selection and fragmentation of precursor ions. A tandem mass spectrometer can select precursors in a first mass spectrometer, can collisionally fragment the selected precursors in a collision cell, and analyze the resulting fragments in a second mass spectrometer. In such data dependent analyses (DDA), groupings are made based solely on precursor ion selection in the first mass spectrometer. However, multiple originating molecules can have chromatographic peaks that overlap in time and have m/z values that lie within the transmission window of the first mass spectrometer. In such a case the fragmentation spectrum obtained in the second mass spectrometer will contain fragments from multiple precursors. As a result, conventional techniques can inadvertently group ions that in fact come from two or more distinct originating molecules.

An improved means to group ions is described by U.S. Pat. No. 6,717,130 to Bateman ("Bateman"), hereby incorporated by reference. In Bateman, spectra from precursors and fragments are obtained using a high- and low-energy switching protocol applied as part of an LC/MS analysis of a single injection of a peptide mixture. In such data, the low-energy spectra contain ions primarily from unfragmented precursors, while the high-energy spectra contain ions primarily from fragmented precursors. Thus this protocol collects spectra in two modes, a low-energy mode and a high-energy mode.

The output of this protocol for each mode is a series of mass spectra over time. The mass spectra can be combined in time to produce a set of selected ion chromatograms. Selected ion chromatograms can also be referred to as mass chromatograms. Hereafter, the terms "selected ion chromatogram" and "mass chromatogram" are used interchangeably. The selected ion or mass chromatograms can be searched for chromatographic peaks. The peaks identify likely ions. Each ion is described by its apex retention time, mass-to-charge ratio, and intensity. Co-pending PCT Application No. PCT/US05/04180, filed Feb. 11, 2005, entitled "Apparatus and Method for Identifying Peaks in Liquid Chromatography/Mass Spectrometry Data and for Forming Spectra and Chromatograms," (the "'4180 Application"), hereby incorporated by reference, describes a two-dimensional convolution technique that can be applied to such spectra to obtain lists of ions and each ion's apex retention time, mass-to-charge ratio, and intensity.

Thus, the output of the LC/MS system is an inventory, or list, of precursor and fragment ions, each ion described by their apex retention time, mass-to-charge ratio, and intensity. The low-energy mode produces a list of ion seen in low energy that contains primarily unfragmented precursor ions. The high-energy mode produces a list of ion seen in high energy that contains primarily fragmented precursor ions.

Bateman describes how ion groupings can be made based solely upon retention time of the chromatographic peaks as seen in mass chromatograms. The '4180 Application describes how ion groupings can be made based solely upon the retention time of ions.

Two ions that have different retention times must derive from different originating molecules. Thus grouping based on retention time can eliminate ions that elute within a chromatographic peak width of a precursor. By requiring that ions in a group must have the same retention time, the methods of Bateman and the '4180 Application-will exclude ions that have different retention times even if their peaks overlap chromatographically.

However, in complex mixtures, it may yet be that multiple originating molecules still elute at essentially the same retention time. As a result, even the improved method described in Bateman and the '4180 Application, which group ions solely on the basis of retention time, can inadvertently group ions that in fact come from two or more distinct eluting molecules.

BRIEF SUMMARY OF THE INVENTION

In an LC/MS experiment, a molecule that elutes from a chromatograph can give rise to multiple ions. We refer to such molecules that are separated chromatographically and elute from a column as originating molecules. The chromatographic profile of an originating molecule determines the chromatographic profile of all the ions that it gives rise to. Thus ions derived from such a molecule must all have the same retention time and must all have the same chromatographic peak shape.

An originating molecule can be ionized in, for example, and electrospray source, and when ionized such a molecule can be detected by the mass spectrometer. The ion corresponding to the originating molecule is generally termed a precursor ion. Examples of precursors can be large molecules such as proteins, or peptides, or small molecules such as the products of metabolism.

A precursor ion can be fragmented by any number of mechanisms. Such fragmentation can take place in the source, or can be induced in a collision cell. Such molecular fragments can be measured by the mass spectrometer. Fragments can be fragmented, giving rise to, in principle, N generations of ionized molecules, all of which can be detected by the mass spectrometer. The precursor or any of the fragments can appear in one or more charge states, and a molecule in each charge state can appear in one or more isotopic masses. Thus, the originating molecule can give rise to one or many ions, each of which can all be detected by the mass spectrometer.

The chromatographic retention time exhibited by each of these ions and the chromatographic peak profile exhibited by each of these ions must exactly reflect both the retention time and peak shape of the originating molecule. (Hereafter, retention time is understood to be chromatographic retention time, and peak shape is understood to chromatographic peak shape.) The measured retention times and peak shapes of ions can deviate from the retention time and peak shape of their originating molecule, but these deviations must result only from the irreducible measurement error or from interference due to unrelated ions. Any such differences cannot arise from an intrinsic difference in retention time or peak shape between an ion and its originating molecule. Thus, the retention time and peak shape of the precursor ion and its fragment ions are intrinsically identical to each other and to the retention time and peak shape of the originating molecule.

Embodiments of the present invention employ this correspondence in chromatographic retention time and in chromatographic peak shape of precursors and fragments that derive from a common originating molecule. Using this correspondence, embodiments of the present invention group ions detected in an LC/MS experiment that are related in retention time and peak shapes.

In operation, given a list of ions and their properties (retention time, mass, and intensity) and their chromatographic profiles, embodiments of the present invention find those groups of ions that share a common retention time and peak shape. Ions are grouped both by retention time and peak shape. An ion is excluded from a particular grouping if either its retention time or its peak shape does not correspond to the retention time or peak shape of ions in that group. In particular, a difference in peak shape excludes an ion from a particular grouping, even if the ion shares the same retention time as ions in that group.

The use of peak shape in addition to retention time when determining proper ion grouping is important because two different originating molecules can elute with the same retention time. Methods, which group ions based solely on retention time, would group these molecules together. If their peak shapes differ, then taking their peak shape into account, embodiments of the present invention can determine that two molecules do not derive from a single eluting molecule, despite their common retention times, but rather derive from two or more distinct eluting molecules.

According to embodiments of the present invention, peak shapes are be compared by pattern matching algorithms to determine if two ions have the same or different peak shapes. Ions that have the same or consistent retention time but inconsistent peak shape are deemed to be from different eluting molecules, and will not be grouped. Ions that have consistent retention times and consistent peak shapes can be from the same eluting molecule, and can be grouped. Embodiments of the present invention employ peak shape in conjunction with retention time to exclude ions that cannot be from a common originating molecule.

Embodiments of the present invention analyze a sample with and LC/MS system and obtain a list of ions detected in that sample. An ion is described by its retention time, mass-to-charge ratio, and intensity. In LC/MS analysis, molecules can undergo fragmentation to result in molecules that are fragments of the originating molecule. Such fragmentation can occur in the source or can be deliberately induced in a collision cell. Regardless of their origin, such fragment ions must also yield chromatographic peaks that are identical in both retention time and peak shape to each other and to the originating molecule.

In addition to producing distinct molecular fragments, molecules such as peptides can produce multiple ions from the originating molecule and from each such fragment. These ions, common to the same molecule, may differ in isotopic mass and charge state. Again, such ions must produce chromatographic peaks that are identical in both retention time and peak shape to each other and to the originating molecule.

After analysis of a sample by LC/MS, embodiments of the present invention identify a cluster of ions by first selecting a reference ion by one of a variety of possible rules. The rules generally are optimized to pick a reference ion that is likely to be a precursor ion corresponding to an originating molecule.

In order to cluster groups of ions with the reference ion, the method then selects ions whose retention times are essentially the same as the reference. After clustering ions based on retention time, embodiments of the present invention compare peak shapes of the ions in the group to the reference. Those ions with whose peaks shapes are measurably different from the reference peak shape are excluded. This peak shape comparison can be implemented by one of a variety of algorithms including, for example, least-squares fitting techniques, neural networks, or other pattern matching algorithms. Once ions whose shapes do not match the reference are excluded, the remaining ions, which match in retention time and in peak shape, can be stored in a database of such groupings. The ion list can then be consulted to see if there is another grouping.

After picking a reference ion, additional requirements can be applied to further restrict the ions in the group. For example, ions may be rejected based upon mass or intensity. For example, ions whose mass or intensity is greater than the mass and intensity of the reference can be excluded.

Ion groupings can be formed without first identifying a reference ion. For example, all peak shapes within a relatively broad retention time window can be analyzed. Further, pattern matching algorithms can be employed that use peak shape comparison alone to find the groupings that best segregate the ions into those groups that have within them the same retention times and peak shapes.

BRIEF DESCRIPTION OF THE DRAWINGS

FIG. 3 is a table that numerically represents the chromatographic peaks associated with each of the entities in the table in FIG. 2 according to an embodiment of the present invention.

FIG. 5 is a table in which intensity data associated with each peak are listed in separate mass chromatograms (rows) according to an embodiment of the present invention.

FIG. 13 is a table listing amino acid sequence information corresponding to an analyzed *E. coli.* sample according to an embodiment of the present invention.

FIG. 14 is another table listing amino acid sequence information corresponding to an analyzed *E. coli.* sample according to an embodiment of the present invention.

DETAILED DESCRIPTION OF THE INVENTION

Figure 1:
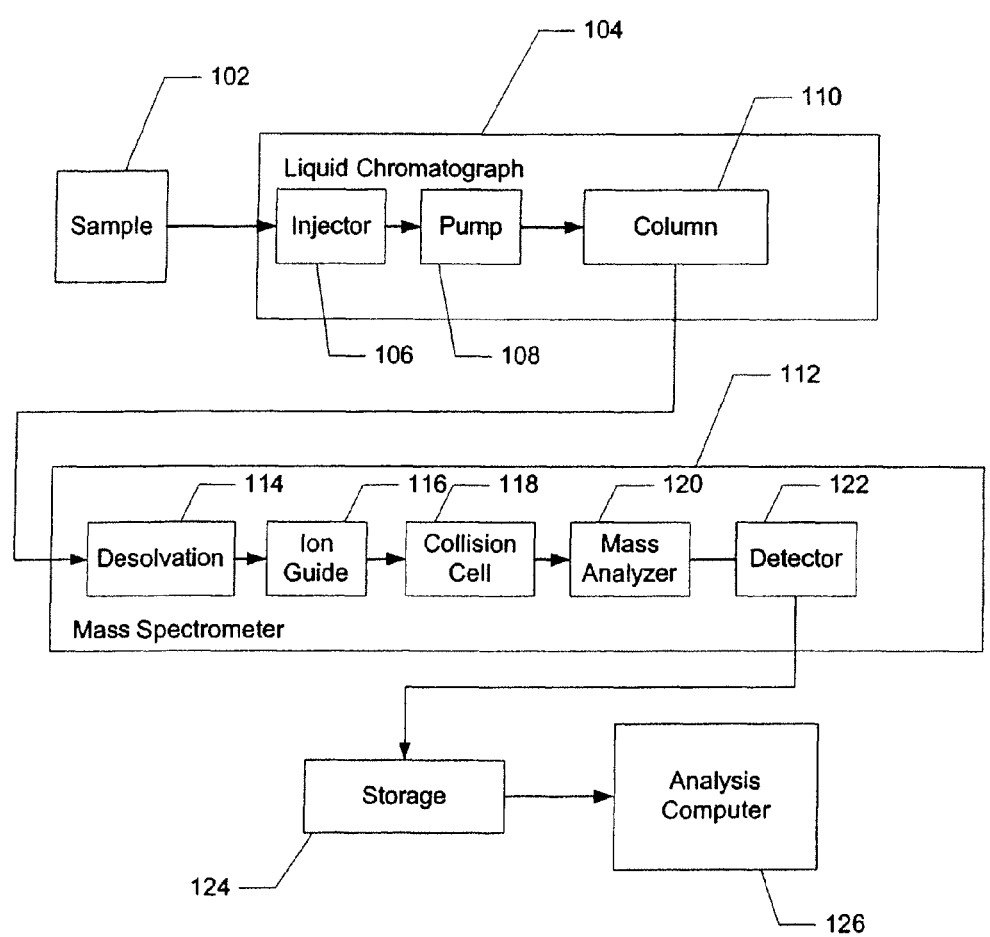
FIG. 1 is a schematic diagram of an LC/MS system for obtaining mass chromatograms according to an embodiment of the present invention.

FIG. 1 is a schematic diagram of an LC/MS system for obtaining mass chromatograms according to an embodiment of the present invention. An LC/MS experiment provides responses or intensities as a function of time and mass. A sample 102 is injected into a liquid chromatograph 104 through an injector 106. A pump 108 pumps the sample through a column 110 to separate the mixture into component parts according to retention time through the column.

The output from the column is input to a mass spectrometer 112 for analysis. A mass spectrometer, such as mass spectrometer 112 measures responses, or intensities, as a function of time and mass-to-charge ratio. Initially, the sample is desolvated and ionized by a desolvation/ionization device 114. Any desolvation technique can be employed, including, for example, a heater, a gas, and a heater in combination with a gas or other desolvation technique. Ionization can be by any ionization techniques, including for example, electrospray ionization (ESI), atmospheric pressure chemical ionization (APCI), or other ionization technique. Ions resulting from the ionization are fed to a collision cell 118 by an ion guide 116. Collision cell 118 can be used to fragment the ions. For example, as described in Bateman an alternating voltage can be applied to the collision cell 118 to cause fragmentation. Spectra are collected for the precursors (no collisions) and fragments (results of collisions).

The output of collision cell 118 is input to a mass analyzer 120. Mass analyzer 120 can be any mass analyzer, including quadrupole, time-of-flight (TOF), ion trap, magnetic sector mass analyzers as well as combinations thereof. A detector 122 detects ions emanating from mass analyzer 122. Detector 122 can be integral with mass analyzer 120. For example, in the case of a TOF mass analyzer, detector 122 can be a microchannel plate detector that counts intensity of ions, i.e., counts numbers of ions impinging it to form. A storage medium 124 provides permanent storage for storing the ion counts for analysis. For example, storage medium 124 can be an internal or external computer disk. An analysis computer 126 analyzes the stored data. Data can also be analyzed in real time without requiring storage in a storage medium 124. In that case, detector 122 passes data to be analyzed directly to computer 126 without first storing it to permanent storage.

Collision cell 118 performs fragmentation of the precursor ions. Fragmentation can be used to determine the primary sequence of a peptide and subsequently lead to the identity of the originating protein.

Collision cell 118 includes a gas such as nitrogen. When a charged peptide interacts with gas atoms, the resulting collisions can fragment the peptide by breaking it up at one or more characteristic bonds. The most common resulting fragments are described as Y- or B-ions. Such fragmentation can be accomplished as on-line fragmentation by switching the voltage in a collision cell between a low voltage state (low energy) which obtains MS spectra of the peptide precursor, with a high voltage state (high energy) which obtains MS spectra of the collisionally induced fragments of the precursors. High and low voltage are referred to as high and low energy, since a voltage is used to impart kinetic energy to an ion.

An LC/MS experiment can produce as one of its outputs a mass chromatogram. A mass chromatogram is a set or group of responses (intensities) recorded as a function of time at a specific mass value. In a mass chromatogram, the mass value may be the central value within a range. That is, the intensity at a given time may be obtained by combining intensities collected over a specified range of mass values. Typically, a mass chromatogram contains one or more chromatographic peaks.

A single molecule, or chemical entity, has a specific mass. In an LC/MS experiment the ionized form of that molecule is observed as a chromatographic peak at the mass value of that ion divided by its charge (mass-to-charge ratio). A chromatographic peak has a peak profile, or elution profile. The chromatographic peak profile can be characterized using several features, including an apex retention time, a peak width, a lift off time and a touch down time. A chromatographic peak width can be described as a width at a specific peak height (FWHM, width at 50% height), or a width between inflection points, or as a standard deviation. The apex intensity or chromatographic peak height is the maximum intensity found in a chromatographic peak profile. Generally, the apex intensity is baseline corrected.

A molecule in an eluent that is separated by a chromatographic separation, and elutes from the column is referred to as the common eluting molecule or originating molecule. The originating molecule is ionized through the ionization source of the mass spectrometer. The resulting ions are measured in an LC/MS or LC/MS$^E$. As a result of isotopic composition and or fragmentation processes, each originating molecule can give rise to multiple categories of ions, each having a unique value of mass and charge. The ion corresponding to the originating molecule is termed the precursor ion, or just the precursor. In peptide digests the originating molecule is a peptide and the ion corresponding to the peptide is referred to as the precursor. Any ion derived from the originating molecule, whether the processor or a fragment, must have the same retention time and chromatographic peak profile as the precursor.

In an LC/MS experiment an ion can be described and/or referred to by its retention time, mass-to-charge ratio, and intensity. A single molecule can appear in an LC/MS chromatogram as a cluster of ions. A peptide gives rise to one or more ion clusters. Each cluster corresponds to a different charge state (e.g., Z=1 or Z=2). Each ion in a cluster corresponds to a different isotopic composition of the peptide. In a cluster of ions from a common peptide, the monoisotope is the ion having the lowest mass, where all the isotopes are in their most abundant, low mass state. Since the ions in the cluster come from a common originating molecule, they must share a common retention time and peak profile.

An originating molecule can give rise to multiple ions due to isotope and charge effects. Additional, important sources of ions are fragments of the originating molecule. These fragments arise from processes that break up the originating molecule. These processes can occur in the ionization source or in a collision cell. Because fragment ions derive from a common eluting, originating molecule, they must have the same chromatographic retention time and peak profile as the originating molecule.

Generally, if an originating molecule gives rise to N ions, and if these are adequately resolved by the mass spectrometer, then there can be N mass chromatograms, where each mass chromatogram contains a peak, a chromatographic profile of an ion that derives from the originating molecule. The retention time and peak profile of each of these N ions will be identical. The term common-retention-time-entity refers to all ions of an originating molecule that, in an LC/MS separation, give rise to chromatographic peaks all having the same retention times and peak shapes.

The retention time and peak shapes of ions that derive from a common originating molecule are the same because the time of ion formation, fragmentation, and ion detection is generally much shorter then the peak width of the originating molecule. For example, a typical chromatographic peak width, measured at full-width at half-maximum (FWHM) is 5 to 30 seconds. The time of ion formation, fragmentation, and detection is typically sub milliseconds. Thus on a chromatographic time scale, the time of ion formation is an instantaneous process. It follows that differences in observed retention times of the ions that derived from an originating molecule is effectively zero. That is, sub-millisecond retention time differences between ions that derived from an originating molecule are small compared to the chromatographic peak width.

The ions that are associated with an originating molecule fall into one of several categories. An ion derived from an originating molecule can be a precursor, a fragment of the precursor, or a fragment of a fragment, or a neutral loss of any of the above masses. Any of these masses can be seen in one or more discrete isotopic states; and in one or more charge states.

In the case of peptides, a given peptide is generally seen to be a cluster of ions, each in a distinct isotopic state, and each in one or more charge states. Ideally the ionization source produces precursors that are a protenated form of the neutral originating molecule. One or more protons can be attached to the neutral molecule and thus the precursors can be one or more mass units higher than the neutral with charge Z=+1, or +2, etc. In practice, this precursor (termed mwHPlus) may be accompanied by lower mass entities that result from the loss of neutral molecules such as water, ammonia, or phosphate. Fragmentation can occur in the source, yielding, typically, Y- or B-ions. Fragmentation can be also be deliberately induced by down-stream interactions with gas molecules in a collision cell.

Embodiments of the present invention cluster groups of related ions from a heterogeneous mixture of ions that co-elute, based on their characteristic, chromatographic peak profiles. For example, in a typical LC/MS experiment (conducted in low-energy mode), embodiments of the present invention match ions of different charge-states to the same parent precursor component, with or without high mass precision or resolution. Furthermore, in instances where the precursor molecule(s) are labile enough to disassociate at a single energy (e.g., low-energy), embodiments of the present invention can cluster all observed charge-states of all related ions (whether they be precursors or in-source fragments) to an originating parent precursor component.

With respect to ions that are generated from collision-induced disassociation of intact precursor ions, embodiments of the present invention can cluster the correct fragment ions to a parent precursor component. This clustering is accomplished without requiring the instrument to pre-select a single precursor for subsequent fragmentation using the mass spectrometer in a High-Low Data Acquisition Mode. More specifically, embodiments of the present invention can cluster associated ions in their appropriate groups when multiple precursors are fragmenting simultaneously, at essentially the same retention time. Thus, embodiments of the present invention can assign fragment ions to their respective precursor when there is more than one precursor fragmenting at the same moment in time. The capabilities of embodiments of the present invention represent an advance over conventional LC/MS/MS, DDA technology, which must assign all detected ions to a precursor. Moreover, embodiments of the present invention can significantly reduce the computational burden for de-isotoping and charge-state reducing ions to their common, singly charged annotation (i.e. MH+).

The method of the current invention can be applied to mixtures other than that of peptides, provided originating molecules give rise to precursor ions and fragment ions. Thus embodiments of the present invention can be used in proteomics, metabolomics, and metabonomics.

The retention time and chromatographic peak profile of a molecule (peptide, metabolite, natural product) eluting from a chromatographic support matrix, such as column 110, is a function of the physical interaction of that molecule between the support matrix and mobile phase. The degree of interaction that a molecule has between the support matrix and the mobile phase dictates the chromatographic profile and retention time for that molecule. In a complex mixture, each molecule is chemically different. As a result, each molecule can have a different affinity for the chromatographic matrix and the mobile phase. Consequently, each can exhibit a unique chromatographic profile.

Generally, a chromatographic profile for a specific molecule is unique and describes the physicochemical properties of that molecule. As described above, parameters used to describe the chromatographic peak profile of a given molecule include the time of initial detection (liftoff), normalized slope, the time of inflection points relative to the time of the peak apex, the time of maximum response (peak apex), the peak width, at inflection points, at full-width-at-half-maximum (FWHM), peak shape asymmetry, and the time of the final detection (touch down) to name only a few.

Figure 2:
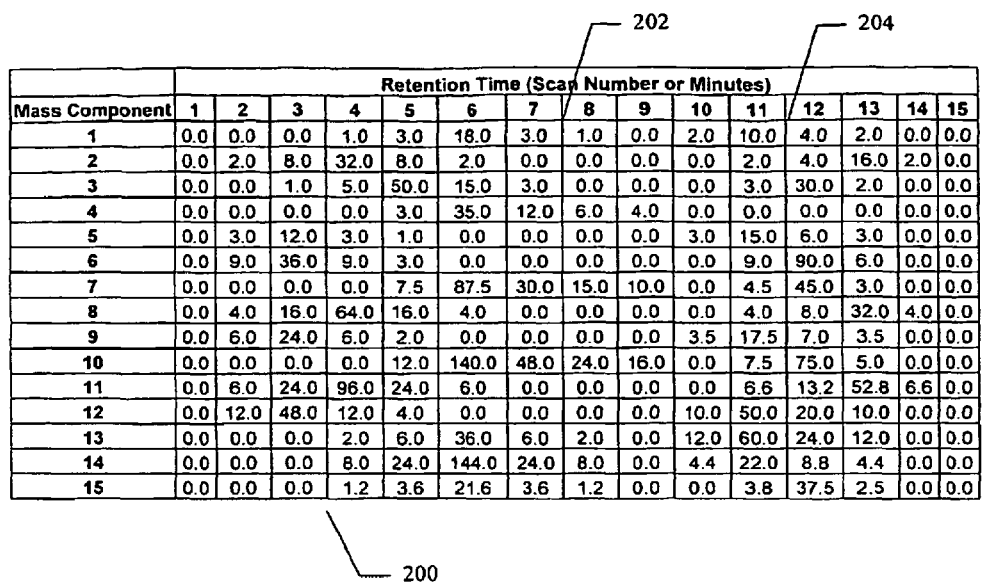
FIG. 2 is a table summarizing the results of a hypothetical LC/MS experiment according to an embodiment of the present invention.

To help describe embodiments of the present invention, analysis of the data of a hypothetical LC/MS experiment is performed according to an embodiment of the present invention. In the hypothetical experiment, it is assumed that some chemical components that are labile and simultaneously generate associated ions (fragments) during the LC/MS data acquisition. Other chemical components are not labile, and only generate a single, intact mass specific to the originating chemical component. In the hypothetical experiment, the LC/MS data acquisition collects 15 spectral scans. FIG. 2 is a table 200 summarizing the results of the hypothetical LC/MS experiment for the 15 spectral scans. The times associated with the scans correspond to columns 1-15. Masses associated with components correspond to the rows 1-15. Ions are detected by detector 122. Detections in each scan and at each mass are indicated in table 200 by responses (intensities) that are greater than zero.

The intensities measured in the 15 spectral scans in the time domain are clustered in mass such that the identical mass measurements (within a specified mass tolerance, e.g., 5 ppm) are clustered to produce each row in table 200. Thus, each row in table 200 corresponds to a group of ion detections with substantially the same measured mass values.

Although these mass measurements may be identical, within a specified mass tolerance, mass describes only one physical characteristic of the molecule. For example, the first row of table 200 shows intensity values that are clearly related to two chemical entities. The intensities for the two chemical entities appear as two chromatographic peaks having the same mass value (in the same row of table 200). The two chromatographic peaks are indicated by boxes 202 and 204 in FIG. 2, and are labeled 1 and 2 in boxes 302 and 304 in FIG. 3).

Each row in table 200 is a mass chromatogram. The mass chromatogram in table 200 demonstrates that chromatographic apex is an additional physicochemical characteristic that can be used to discriminate between the two individual components. The chromatographic apex retention time is the point at which the chromatographic intensity profile of an entity is at its maximum during an LC/MS data acquisition. The differing apex retention times of the two molecules reflect the different physical interaction of the chemical entities to the specific column resin (i.e., hydrophobicity, hydrophilicity, or polarity).

Taking into account chromatographic apex retention times, the 15 individual mass chromatograms (rows) in table 200 actually contain 29, independent and distinguishable, chemical entities. FIG. 3 is a table 300 that numerically represents the chromatographic peaks associated with each of the 29 chemical entities. As shown in table 300, the chromatographic peaks are identified by an arbitrarily assigned one-up numbers in the rows. Consequently, peaks indicated by boxes 302 and 304 correspond to peaks represented by boxes 202 and 204 in table 200 respectively.

If the chemical entity is labile, the resulting fragment ions that are simultaneously generated during the LC/MS acquisition appear as a set of chromatographic peaks. Because these peaks originate from a common eluting parent molecule, they must share a common retention time and must have the same chromatographic peak profile. This is true for fragment ions produced during the high energy portion of the alternating high/low energy patter in collision cell 118. If the chemical entity is not labile, a single mass only appears in the data as a single chromatographic peak. That single profile describes the single, intact chemical entity.

As indicated by their respective intensity distributions in table 200, the apex retention times of chromatographic peaks 7, 12 and 18 (table 300) are the same. Because this set of chromatographic peaks share a common apex retention time, they likely derive from a common eluting molecule. Similarly, chromatographic peaks 1, 24, 26, and 28; share a common apex retention time, as seen by their respective intensity distributions in table 200. Note that even though the bodies of these seven peaks overlap, their different apex retention times indicate that these peaks fall into two groups corresponding to two distinct originating molecules. Peak 5 in table 300 appears to be a single mass, having no apex retention time in common with any other chromatographic peak. Thus, Peak 5 is deemed to be the only peak in the data associated with its originating molecule.

Although mass and retention time may be sufficient to cluster components into groups in a simple mixture, mass and retention time alone may not be sufficient for clustering components in a complex mixture. Complex mixtures can contain many originating molecules that elute at substantially the same (indistinguishably different) retention times. Consequently, additional distinguishing criteria may be required for complex samples.

Embodiments of the present invention can extract additional information from LC/MS data to use to further characterize components that elute at the same moment in time. In addition to apex retention time, for example, the shape of the chromatographic profile associated with each chromatographic peak can be analyzed to better cluster molecules into groups. The use of retention time alone allows clustering of chromatographic peaks into groups. The additional use of the chromatographic profile of each chromatographic peak allows further distinguishing between peaks that have identical (indistinguishably different) retention times, but should be associated with different originating molecules.

Figure 4:
FIG. 4 is a table showing normalized intensity data corresponding to the intensity data shown in FIG. 2 according to an embodiment of the present invention.

An example is provided to help explain the use of chromatographic peak profiles. FIG. 4 illustrates a table 400 in which the intensities for each of the 29 chromatographic peaks in table 200 are normalized to the maximum, apex intensity of the respective peak. Normalizing peak-intensity data scales the intensities so the respective profiles can be compared for similarity.

FIG. 5 illustrates a table 500 in which the chromatographic peaks within each mass chromatogram listed in table 400, are separated such that each chromatographic peak is listed in a separate row. In the first column of table 500, the 29 peaks are identified by their one-up numbers (table 300), and the row of the mass chromatogram from table 400 in parenthesis. Each row in table 500 contains a single chromatographic peak, which corresponds to a unique mass component (ion) in the data.

By organizing the chromatographic peaks in this fashion, the profile for each chromatographic peak can be analyzed independently. The mass chromatogram in row 1, from table 400, contains two discrete peaks, 1 and 2, as indicated in rows 1 and 2 of table 500. It can be seen from table 500 which chromatographic peaks are likely associated with one another. For example, peaks 3(2), 14(8) and 20(11) (peaks 3, 14, and 20 of FIG. 2) are associated with one another. Similarly, peaks 7(4), 12(7) and 18(10) (peaks 7, 12, and 18 in FIG. 2) are associated with one another.

As described below, chromatographic peaks can be automatically clustered by not only their apex retention times, but also by their corresponding chromatographic peak profiles or chromatographic peak shapes. Using the peak shape information allows more confidence when clustering peaks found in more complex data sets such as digests of E. coli and of human serum.

Figure 6:
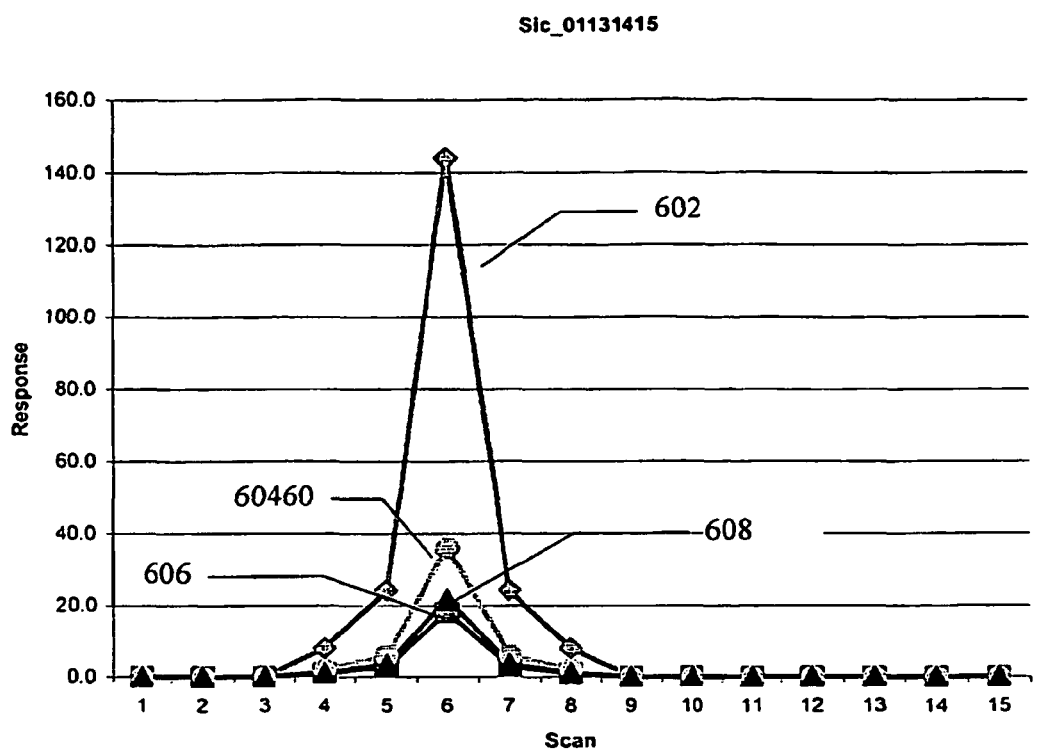
FIG. 6 is a plot of unnormalized mass chromatograms corresponding to peaks 1, 24, 26 and 28 in FIGS. 2 and 3 according to an embodiment of the present invention.

FIG. 6 is a plot of normalized mass chromatograms (table 200) corresponding to peaks 1 (item 606), 24 (item 604), 26 (602) and 28 (item 608) of FIG. 2. As can be seen in FIG. 6, each chromatogram reaches a maximum response at scan 6.

Figure 7:
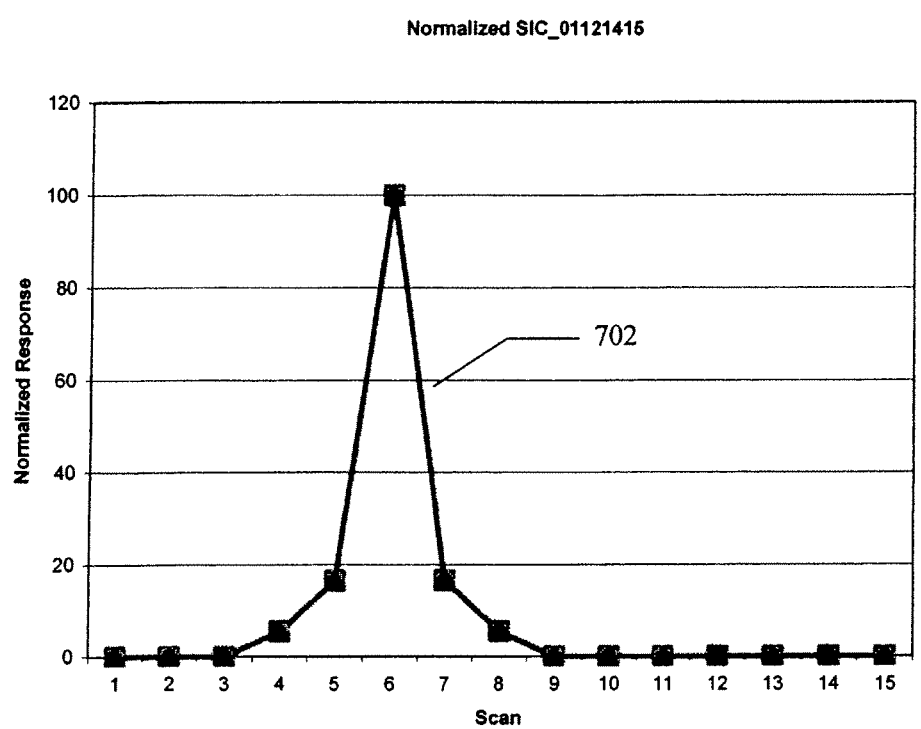
FIG. 7 is a plot of the normalized mass chromatograms corresponding to the data plotted in FIG. 6 according to an embodiment of the present invention.

FIG. 7 is a plot of the normalized mass chromatograms (table 500) plotted in FIG. 6. As described above each component of the peak is normalized with respect to the maximum response value of the respective peak. Normalization scales the response measurements across each of the components allowing direct comparison of the resulting peak shapes to determine whether the profiles are identical or are different. If the profiles are different, they cannot arise from the same originating molecule. If they are the same (or essentially indistinguishable) then the respective ions giving rise to the indistinguishable chromatographic peaks are deemed to be from the same originating molecule.

As can be seen in FIG. 7, the chromatographic profiles corresponding to peaks 1, 24, 26 and 28 overlap (item 702). Because they are identical, it can be concluded they all come from the same originating molecule. Not only do these mass components have profiles that apex at the exact same moment in time, but also they have the same normalized chromatographic profile (peak shape) as shown by the overlapping peaks 702.

Figure 8:
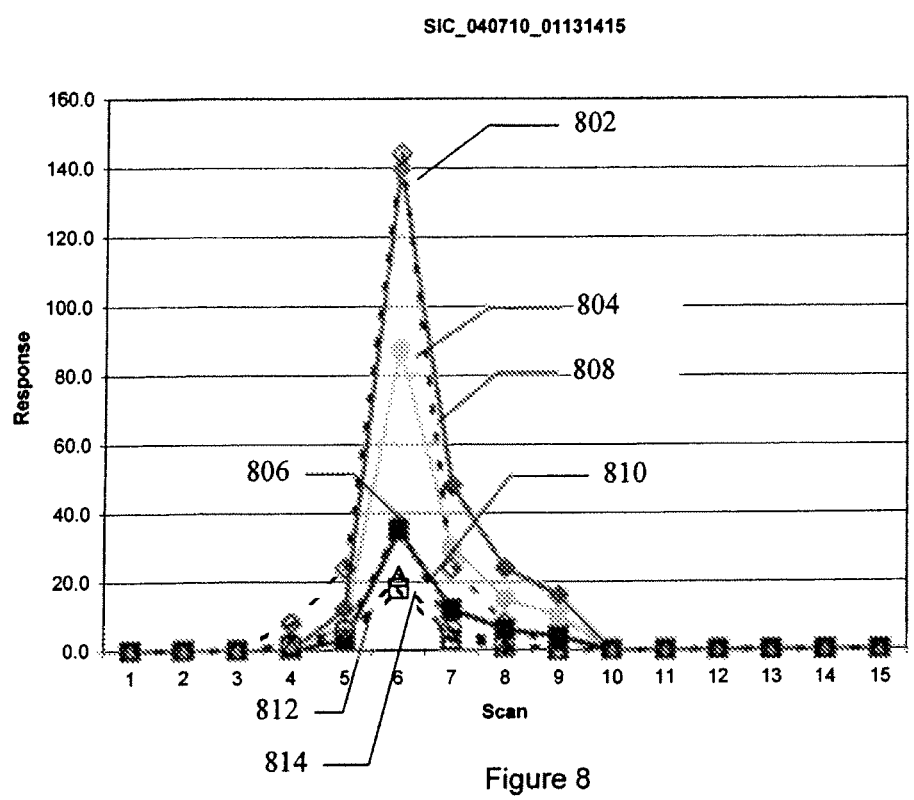
FIG. 8 is an overly plot of the unnormalized intensity responses associated with the peak 1, 7, 12, 18, 24, 26 and 28 of FIGS. 2 and 3 according to an embodiment of the present invention.

Embodiments of the present invention can also be used to resolve chromatographic peaks that coelute and apex at the same moment in time. FIG. 8 is an overlay plot of unnormalized intensity responses corresponding to peaks 7 (item 806), 12 (item 804), and 18 (item 802) (tables 200 and 300) and peaks 1 (item 812), 24 (item 810), 26 (item 808), and 28 (item 814) (tables 200 and 300) plotted against corresponding scan times. Each of the peak chromatograms plotted in FIG. 8 reach their maximum peak apex response at scan 6. Thus, the components are indistinguishable using peak apex retention time alone.

Figure 9:
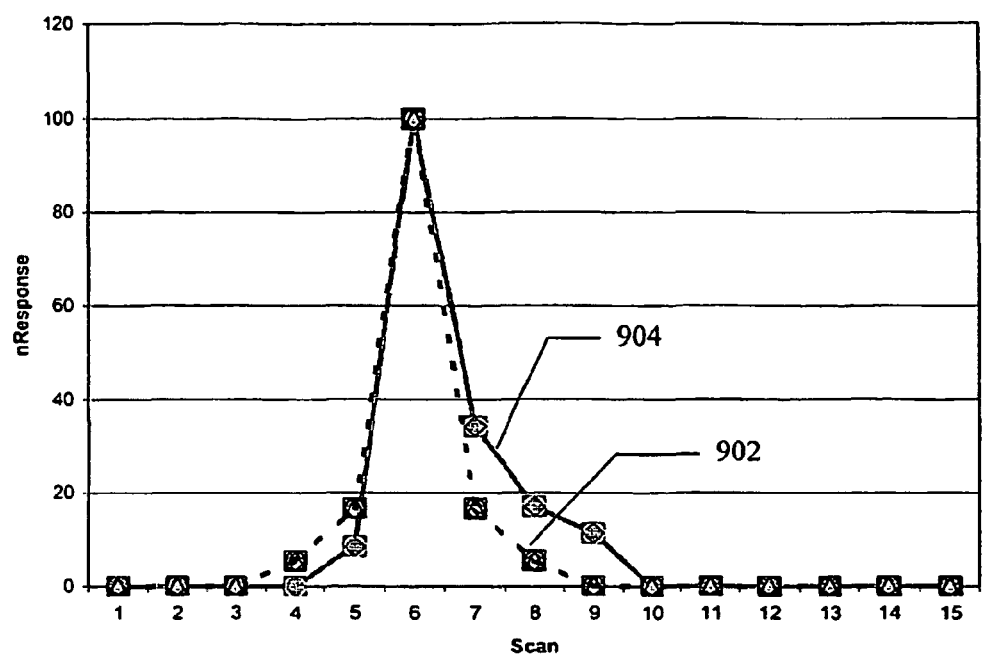
FIG. 9 is an overlay plot of the normalized intensity responses associated with the peaks plotted in FIG. 8 according to an embodiment of the present invention.

However, if peak shape is also considered, the components can be distinguished. FIG. 9 is an overlay plot of the normalized intensity responses corresponding to chromatographic peaks shown in FIG. 8 to facilitate comparison of the chromatographic peak profiles. After normalizing the profiles, two distinct chromatographic profiles 902 and 904 are clearly observable.

After performing the normalization and overlay operation, we can associate the three mass-retention time components 7, 12 and 18 (item 904) are deemed to derive from a common originating molecule and the four remaining mass-retention time components 1, 24, 26 and 28 (item 902) are deemed to derive from a separate, independent originating molecule.

Peak profiles are used to generate a reference peak to which peaks in a group are compared. The reference peak can be a standard peak, such as a predetermined peak, or can be generated from the peaks associated with ions in the retention time groupings. For example, one ion in the group can be chosen arbitrarily as the reference. In addition, an average peak profile can be determined or a median peak profile can be determined from the data associated with the ions in a particular grouping. The peaks in the group can then be compared to the average or median peak.

Other well-known peak shape comparison techniques can be used as well. For example, automated peak shape comparison can be performed using a clustering algorithm such as self-organizing maps (SOMs). Self-Organizing Maps are a special class of artificial neural networks based on competitive learning. The algorithm produces a two-dimensional grid (map), in which similar records appear close to each other, and less similar records appear more distant. From the map it is possible to visually investigate which records are related. Thus, SOMs provide a form of clustering. A description of self-organizing maps is described in Mirkin, B. Mathematical Classification and Clustering, Nonconvex Optimization and Its Applications Volume 11, Pardalos, P. and Horst, R., editors, Kluwer Academic Publishers, The Netherlands. (1996) and in MacQueen, J. Some methods for classification and analysis of multivariate observations (1967), in Le Cam, L. M. and Neyman, J., editors, Proceedings of the Fifth Berkeley Symposium on Mathematical Statistics and Probability. Volume I: Statistics, pages 281-297. University of California Press, Berkeley and Los Angeles, Calif.), both of which are incorporated herein by their entirety.

The mathematical theory governing SOMs is provided in the above-cited references, and is summarized as follows (taken from the description found in DecisionSite documentation in software available from Spotfire of Sommerville, Mass.).

SOMs operate through iterative adaptation. During each iteration a weight factor is calculated that includes a neighborhood function defined by an effective radius. The effective radius at iteration t is given by:

$$r(t) = r(\text{begin}) + \Delta r \cdot t$$

where, $$\Delta r = \frac{r(\text{end}) - r(\text{begin})}{k}$$

where, t=time in number of iterations so far, k=training length (set by user),
r(end)=end radius (set by user), and
r(begin)=initial radius (set by user).

Two neighborhood functions are available in the Spotfire software, a Bubble neighborhood function and a Gaussian neighborhood function. The Bubble neighborhood function for a node j and a winning node i(x) is defined as follows:

$$h_{j,i(x)} = \begin{cases} 1 & \text{if } d_{i,j} \leq r(t) \\ 0 \end{cases}$$

where,
$d_{i,j}$=Euclidean distance between node and winning node.
The Gaussian neighborhood function is defined as follows:

$$h_{j,i(x)} = -\exp\left(\frac{d_{i,j}^2}{2r(l)}\right).$$

Self-organizing maps use a learning factor that decreases over time according to a learning function. The Spotfire software provides two learning functions, an inverse function and a linear function. In the inverse learning function, the learning rate factor at iteration t is provided by:

$$a(t) = a(0)\frac{b}{t+b}$$

where
t=time, number of iterations,
b=training length/100, and
a(0)=initial learning rate (set by user).
In the linear learning function, the learning rate factor at iteration t is provided by:

$$a(t) = a(0)\left(1 - \left(1 - \frac{a(0)}{100}\right) \cdot \frac{t}{trainlen}\right)$$

where
t=time, number of iterations,
trainlen=training length (set by user), and
a(0)=initial learning rate (set by user).

The quality of a particular SOM can be estimated using mapping precision and topology preservation. Mapping precision measures the average quantization error and is calculated in the Spotfire software as follows:

$$\varepsilon_q = \frac{1}{N}\sum_{i=1}^{N} |x_i - w_c|$$

where c is the best matching unit for the actual x. The topographic error is calculated by:

$$\varepsilon_t = \frac{1}{N}\sum_{i=1}^{N} u(x_k).$$

where u is 1 if the first and second best matching units are not in the near vicinity of each other, otherwise us is 0.

Figure 10:
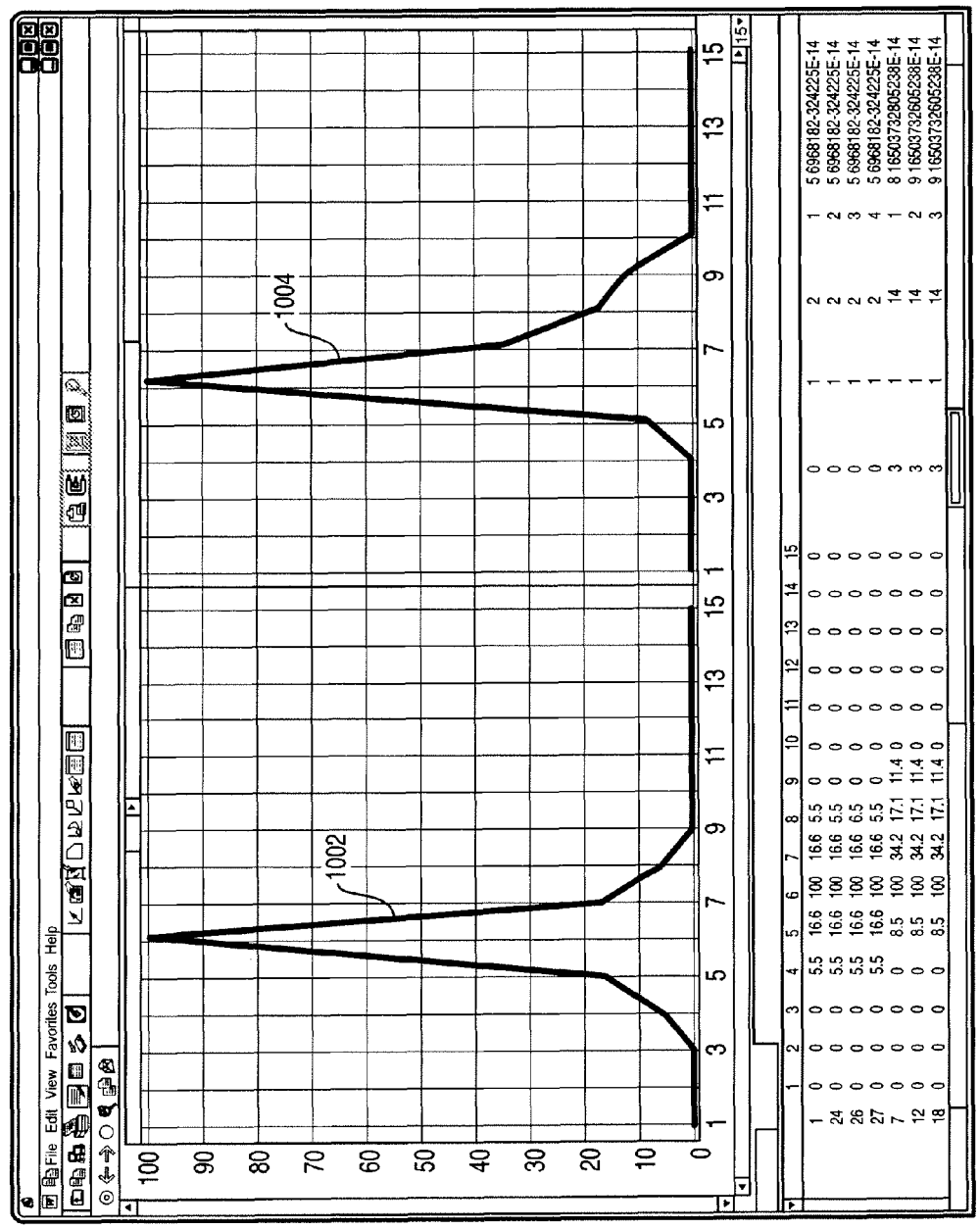
FIG. 10 is a plot showing clustering results after applying SOM analysis to mass components 1, 7, 12, 18, 24, 26 and 28 according to an embodiment of the present invention.

FIG. 10 is a plot showing clustering results after applying SOM analysis to mass components (chromatographic peaks) 1, 7, 12, 18, 24, 26 and 28. The similarity index from the SOM analysis indicates that although these components co-elute at the same moment in time, the associated mass components emanate from two chemical species. The four mass components 1, 24, 26 and 28 (item 1002) have a similarity index of 5.70E-14, while the remaining three mass components 7, 12 and 18 (item 1004) have a similarity index of 9.17E-14.

Figure 11:
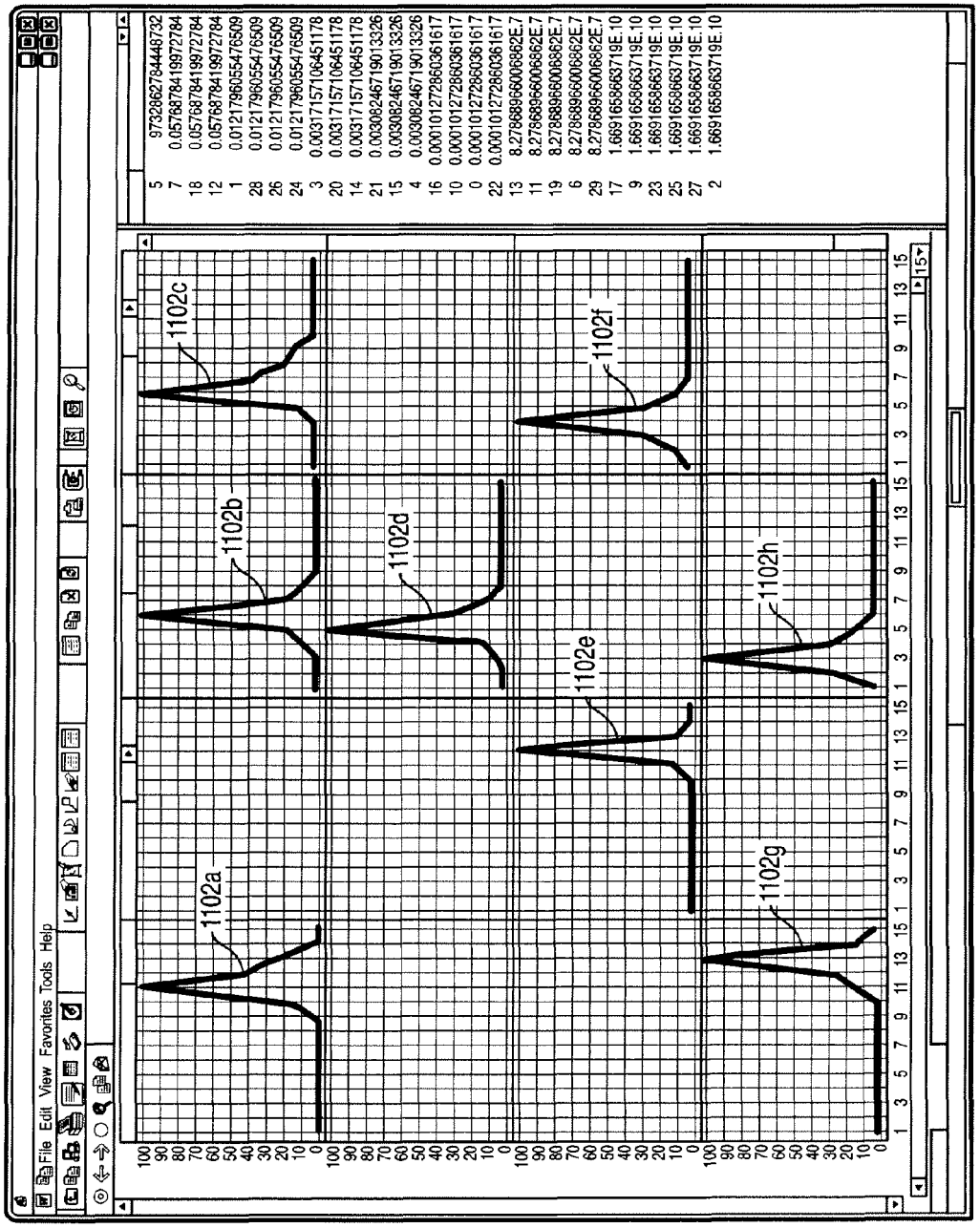
FIG. 11 is a plot of SOM analysis applied to the entire set of 29 chromatographic peaks of the table in FIG. 5 according to an embodiment of the present invention.

FIG. 11 is a plot of SOM analysis applied to the entire data set of 29 chromatographic peaks of table 500. As can be seen in the plot of FIG. 11, SOM analysis associates the 29 chromatographic peaks into 8 distinct clusters 1102 a-h. As a result, the 29 peaks are deemed to derive from 8 separate originating molecules. These results correspond to the same color-coded groups designated in the same table. This is a simple example of using clustering to group components by their overall, chromatographic behavior.

A number of techniques can be used to cluster the peal. In addition to SOMs, these techniques include, without limitation (1) hierarchical clustering as described in Mirkin, B. (1996) Mathematical Classification and Clustering, Nonconvex Optimization and Its Applications Volume 11, Pardalos, P. and Horst, R., editors, Kluwer Academic Publishers, The Netherlands. ("Mirkin"), Sneath, P., Sokal, R. R. (1973) Numerical taxonomy, Second Edition, W.H. Freeman, San Francisco); (2) K-means clustering as described in Mirkin; and (3) principal component analysis as described in Jolliffe, I., T., Principal Component Analysis, Springer. Series in Statistics, New York, Springer-Verlag, 1986.

Figure 12:
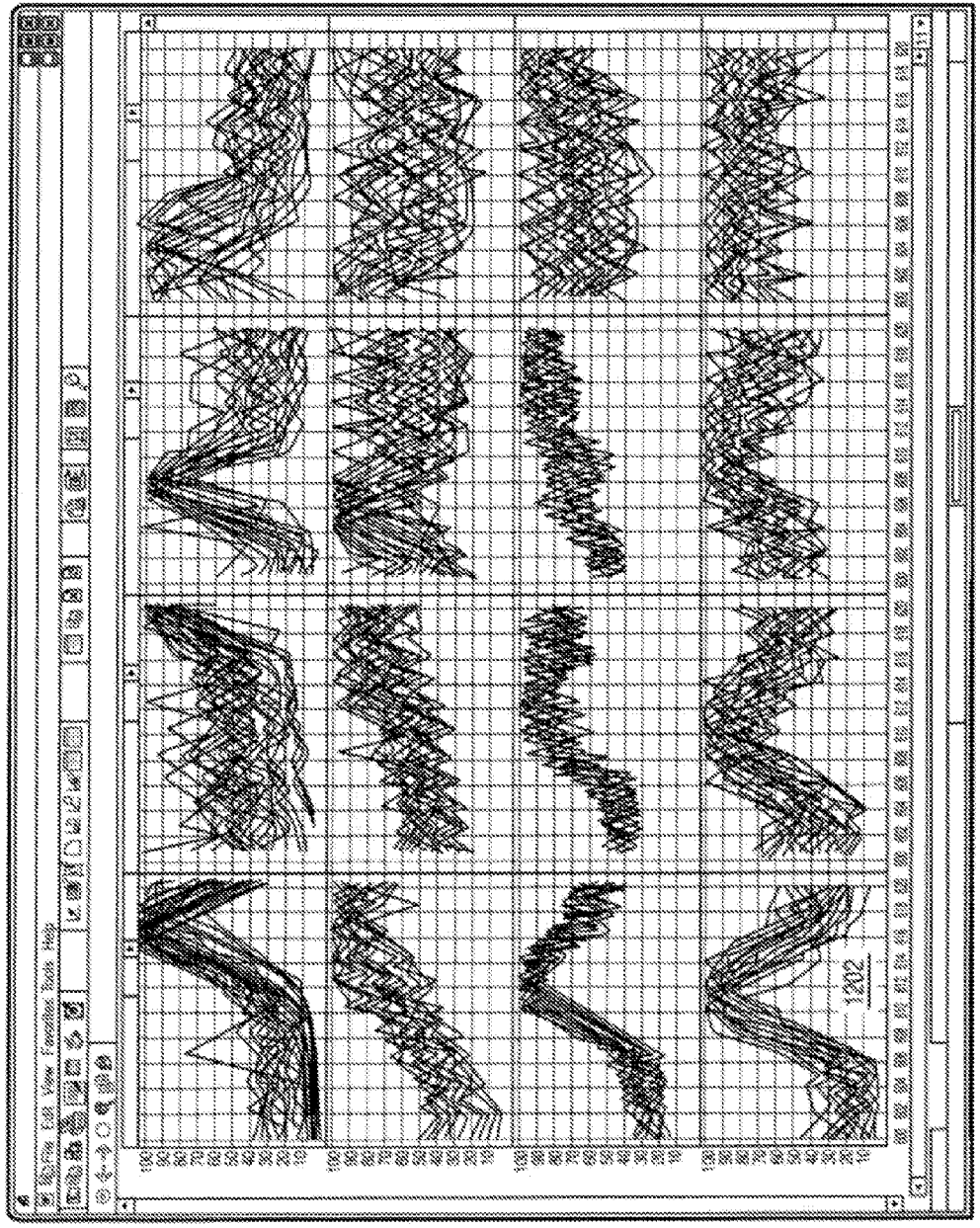
FIG. 12 is a plot showing clustering resulting from SOM analysis applied to chromatographic peak intensity data from an *E. coli.* sample according to an embodiment of the present invention.

As described above, embodiments of the present invention are particularly useful for analyzing complex mixtures, such as digests of *E. coli*. FIG. 12 is a plot showing clustering resulting from SOM analysis of twenty scans (1.5 minutes) of data, consisting of 2582 mass-retention time components of a tryptic digest of *E. coli*. As shown in FIG. 12, the mass-retention time components are segregated into 16 distinct clusters according to the similarities of their corresponding chromatographic profiles.

Another technique for comparing chromatographic peak shapes that can be used in embodiments of the present invention is the chromatographic pattern analysis method described in U.S. Pat. No. 5,969,228 to Gorenstein ("Gorenstein"), hereby incorporated by reference in its entirety. In Gorenstein, two chromatograms obtained from two injections are compared to derive a residual value indicative of difference between a standard and a sample. The technique disclosed in Gorenstein can be applied to two mass chromatograms obtained from the same injection. The methods described in Gorenstein would be applied to the same retention time range in each of the two mass chromatograms. One of the mass chromatograms contains the chromatographic peak profile of the precursor (the standard) and the other mass chromatogram contains the chromatographic peak profile of another peak (the sample) that possibly derives from the originating molecule (e.g., a fragment of the precursor). The method described in Gorenstein is then used to determine if the profile of the second peak is similar to or different from that of the precursor's chromatographic peak profile based on a derived residual value.

As described above, embodiments of the present invention are applicable to LC/MS data collected using a high/low switching protocol such as described in Bateman. Collision cells serve dual-purpose. At low-energy such cell cool, or reduce internal energies of the migrating ions, allowing more ions to enter the downstream mass analyzer. Ideally, such low-energy traversal of the collision cell produces only a more focused beam with no fragmentation. Typical low-energy accelerating potentials are a few volts. If higher voltages are impressed on the collision cell (10 to 30 volts), then in addition to cooling, fragmentation processes occur, breaking the precursors into ionized fragments. In high-low switching (Bateman patent), the switching occurs in an alternating cycle, so that multiple cycles occur within the time scale of a chromatographic peak. As are result, the peak profile of both the low-energy precursors and the high-energy fragments are adequately sampled. It follows that the retention times, chromatographic peak profiles, and intensities of each low- and high-energy ion can be accurately measured along with its mass-to-charge ratio.

As described in Bateman, chromatographic peak profiles can be obtained from mass chromatograms (e.g., selected ion chromatograms) for both low-energy and for high-energy modes of data collection. Thus a chromatographic peak profile can be obtained for each ion detected in low-energy spectra and for each ion detected in high-energy spectra.

Retention time and peak profile comparison can be carried out for ions seen in low-energy and high energy. Retention time and peak profile comparison can be carried out for ions seen in single mode experiments, as well. Such single mode experiments are usually carried out at low (non-fragmenting) energies. But single mode experiments can also be carried out at essentially fixed energy producing a mixture of precursor and fragment ions. The methods described here applied to these single and multi-Mode methods of operating a mass-spectrometer.

In practice, variations between retention time and peak shape of such grouping of ions can arise as a result of one or more non-idealities. All measurements are subject to some form of statistical error. In the case of ion detection by microchannel plates (MCP), the irreducible statistical error is due to counting noise, as described by Poisson statistics. Ideally, all ions collected in the unfragmented mode are of the originating molecules, and ions collected in fragmenting mode are fragments of the respective originating molecule. As described above, all ions of a common, originating molecule must have the same retention time and chromatographic profile. Thus, such ions can be compared by their retention times and peak shapes using the methods described above.

In this manner, data obtained using a high/low switching protocol can be processed to efficiently segregate each accurate mass-retention time component into appropriate groups, such that the mass spectrometric data associated with each bin (both low energy and high energy) contains only those masses emanating from each single, chemical component, i.e., each originating molecule.

The data shown in FIG. 12 was further validated by performing a mass tagging calculation using the list of mass-retention time components in cluster 1202 to obtain the amino acid sequence information listed in tables 1300 in 1400 of FIGS. 13 and 14 respectively. Sequence tagging is the process of identifying a peptide by: 1) taking a set of binned masses and sorting them by decreasing mass, 2) determine the mass differences among the sorted masses, 3) associating specific mass differences to an amino acid residues to create a sequential series of amino acid residues or partial peptide sequence, 3) along with the partial peptide sequence, the light and heavy accurate mass measurement can be used to identify a peptide (see Mann M, Wilm M., Error-tolerant identification of peptides in sequence databases by peptide sequence tags. Anal Chem. 1994 Dec. 15; 66(24):4390-9; Mortz E, O'Connor P B, Roepstorff P, Kelleher N L, Wood T D, McLafferty F W, Mann M. Sequence tag identification of intact proteins by matching tandem mass spectral data against sequence data bases. Proc Nad Acad Sci USA. 1996 Aug. 6; 93(16):8264-7.PMID: 8710858; Shevchenko A, Jensen O N, Podtelejnikov A V, Sagliocco F, Wilm M, Vorm O, Mortensen P, Shevchenko A, Boucherie H, Mann M. Linking genome and proteome by mass spectrometry: large-scale identification of yeast proteins from two dimensional gels. Proc Natl Acad Sci USA. 1996 Dec. 10; 93(25):14440-5. PMID: 8962070).

Figure 15:
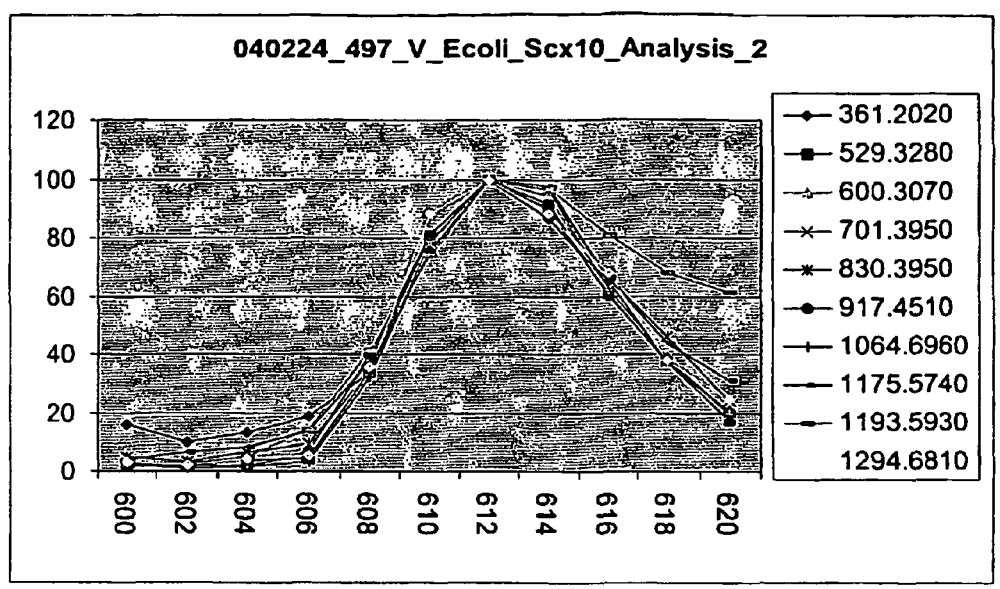
FIG. 15 is a plot of the chromatographic profiles of the y-ions listed in the tables of FIGS. 13 and 14.

The mass tag leads to an unambiguous peptide sequence identification to phosphoglycerate kinase (VATEFSETAPATLK). The peptide identification was verified by the presence of eight contiguous y"-ions, along with a characteristic neutral loss of one of the said y-ions (minus water from glutamic acid residue). FIG. 15 is a plot of the chromatographic profiles of the y-ions listed in tables 1300 and 1400.

Peak comparisons should also take into account sources of noise. For example, sources of error include coelutions or interferences with ions from other originating molecules. Such interferences in mass and retention time, can distort peak shapes, and alter measured values of retention time.

Techniques for accounting for such nonidealities include deconvolving the impurity (effectively removing it) and applying a peak purity method in conjunction with flagging those peaks that are judged to be interfered with. In the case where a peak is either too low in signal to noise to effectively determine its peak shape, or in the case where the peak is interfered with, a suitable flag can be set to signal that the peak shape measurement of a given peak may not be suitable for use in comparison with the precursor peak profile.

Figure 16:
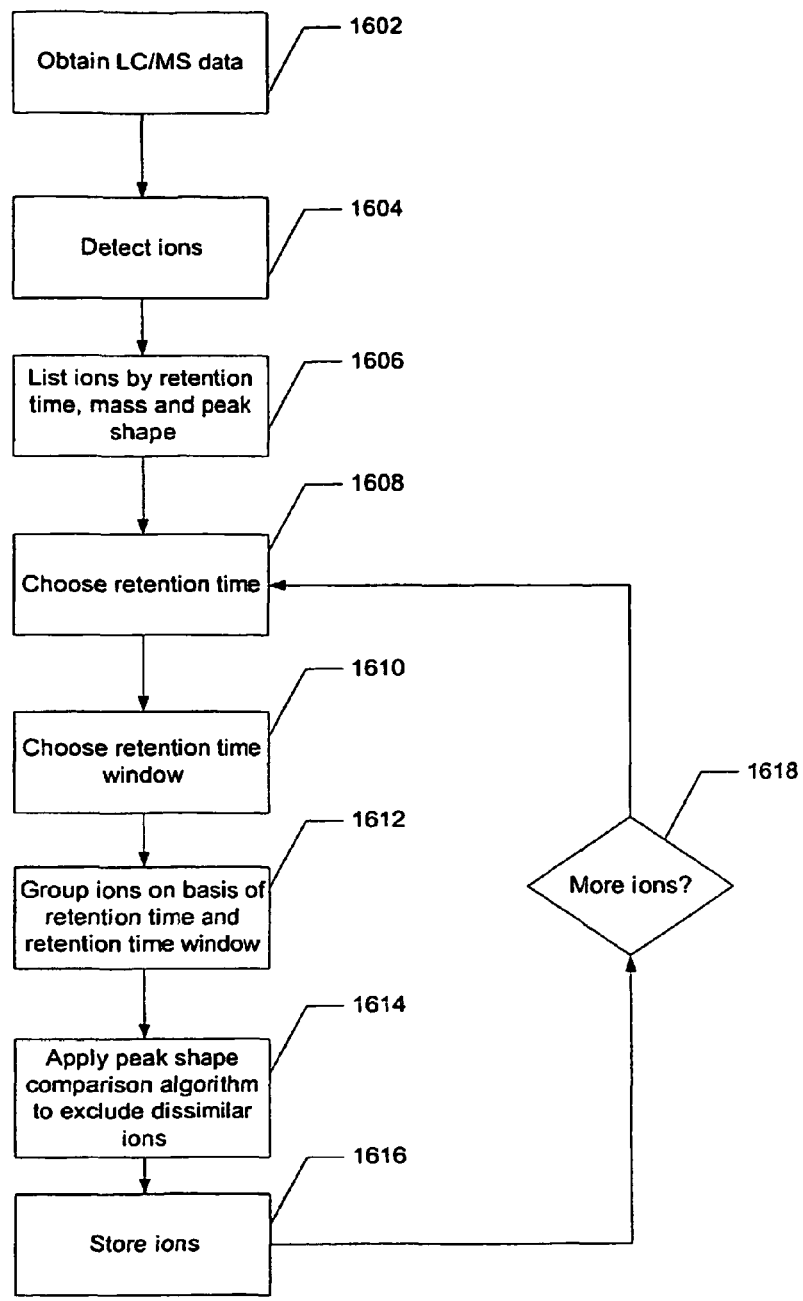
FIG. 16 is flow chart for a method for grouping precursor and fragment ions using selected ion chromatograms according to an embodiment of the present invention.

FIG. 16 is a flow chart for a method for grouping precursor and fragment ions using mass chromatograms (e.g., selected ion chromatograms) according to an embodiment of the present invention. In step 1602 LC/MS data is obtained. Preferably, the LC/MS data is in the form of spectral scans from a single injection of a sample. The sample mixture is separated by a liquid chromatograph and mass analyzed by a mass spectrometer to generate the LC/MS data. In step 1604, ions are detected in the LC/MS data. Once such detection algorithm is described in co-pending PCT Application No. PCT/US05/04180, filed Feb. 11, 2005, entitled "Apparatus and Method for Identifying Peaks in Liquid Chromatography/Mass Spectrometry Data and for Forming Spectra and Chromatograms," (the "'4180 Application") which finds apices within an LC/MS data matrix that has been processed with a 2-dimensional convolution filter.

These ions can also be obtained from a low-energy mode and a high-energy mode as described by Bateman. In each mode, the ions are detected and their properties (retention time, mass-to-charge, and intensity) are obtained by the method described in the '4180 application.

If these ions are from peptides, these ions may be processed further to determine those ions that correspond to the peptide monoisotope, thereby excluding ions that are not monoisotopic ions from a peptide. An example of such processing is described in FIG. 17 of related application WAA-394, and its accompanying text, hereby incorporated by reference. For example, if a peptide appears at charge state 2, it is conventional to retain only the mono-isotope ion, and use the charge state to covert the observed mass-to-charge ratio to a mass value.

For simplification in the following description, the term ion refers to a unique molecule. In addition, if that unique molecule appears at multiple charge or isotope states, it is assumed that a suitable algorithm has been applied so that only one representative ion of the collection of observed ions associated with that unique molecule is retained. Such an algorithm is described in related application WAA-394, hereby incorporated by reference.

In step 1606, a list of ions characterized by their retention time, mass and peak shape is generated. The outputs of ion detection 1604 are retention times, masses (or mass-to-charge ratios), and intensities. In step 1606, the chromatographic peak shape of each ion can be obtained from mass chromatograms (e.g., selected ion chromatograms), where the mass channel is chosen to be coincidence with the mass of the ion. The noise in a mass chromatogram (and the noise in a peak shape obtained from a mass chromatogram) can be reduced by combining mass chromatograms in a well-known manner over a range of mass values that correspond to the mass spectrometric peak width. For example, if a Time of flight mass spectrometer has a mass spectral peak width of 20 millidalton, and 4 millidalton spacing between mass channels, then combining 5 mass chromatograms centered on the mass of the ion will increase the signal, and decrease the noise associated with the points along the mass chromatogram.

In step 1608, a reference retention time is chosen. The reference retention time is chosen using rules driven by mass value, or retention time, or scan number. For example, in an embodiment of the present invention, ions that have a common retention time are initially selected. Ions that do not have a common retention time cannot be from a common originating molecule. Preferably, a central retention time corresponding to a reference ion of interest is chosen. The reference ion can be, for example, an ion that has a known mass that falls within a broad retention time window. Another selection rule is to choose an ion of maximal intensity within a group of ions of interest. Once such a reference ion is picked, its retention time is the reference retention time. The reference retention time is used to define a window of retention time. The retention time window is chosen in step 1610. Preferably, the retention time window is chosen to be about ⅕th of a chromatographic peak width, defined at the full width at half maximum of the peak (FWHM). Thus, if a peak has a FWHM of 30 seconds, then the retention time window is chosen to be +/−3 seconds about the reference retention time. In step 1612, ions associated with the reference retention time are collected. Given the reference retention time and retention time window, all ions that fall within that window are found. Additional rules can be applied to exclude ions that cannot be associated with the chosen ion. For example, only those ions having lower mass and lower intensity than the reference ion may be selected. This rule is consistent with the hypothesis that the reference ion is a precursor or originating molecule, and that all other ions are fragments. At this stage in the method, collected ions have the same retention times, mass values, and intensities such that they are consistent with being fragments of a common originating molecule.

In step 1614, a chromatographic peak shape comparison algorithm is applied. The peak shape comparison algorithm is used to exclude ions not having similar peak shape to the chromatographic peak shape of the reference ion. Alternatively, a peak shape comparison algorithm could be used to exclude ions not having similar peak shapes to the ions in the group. The peak shape comparison algorithm can be any algorithm for comparing peak shapes, such as those described above. At this stage in the processing, the collected ions have the same retention times, mass values, intensities, and peak shapes such that they are consistent with being fragments of a common originating molecule. In step 1616, groups of ions are stored. Every group of ions that have common retention time and peak shape (and that may satisfy other mass and intensity rules) are assumed to derive from a common originating molecule. Such groups are stored in a database for subsequent analysis. The database stores the groups of ions together with other information related to the sample and the LC/MS analysis. Once a set of ions is deemed to be a group, the set of ions can be excluded from consideration in subsequent iterations (steps 1608 to 1616). In step 1618, it is determined whether there are remaining ions to be processed. If so, the method continues in step 1608. If there are no more ions to be processed, the method ends.

Figure 17:
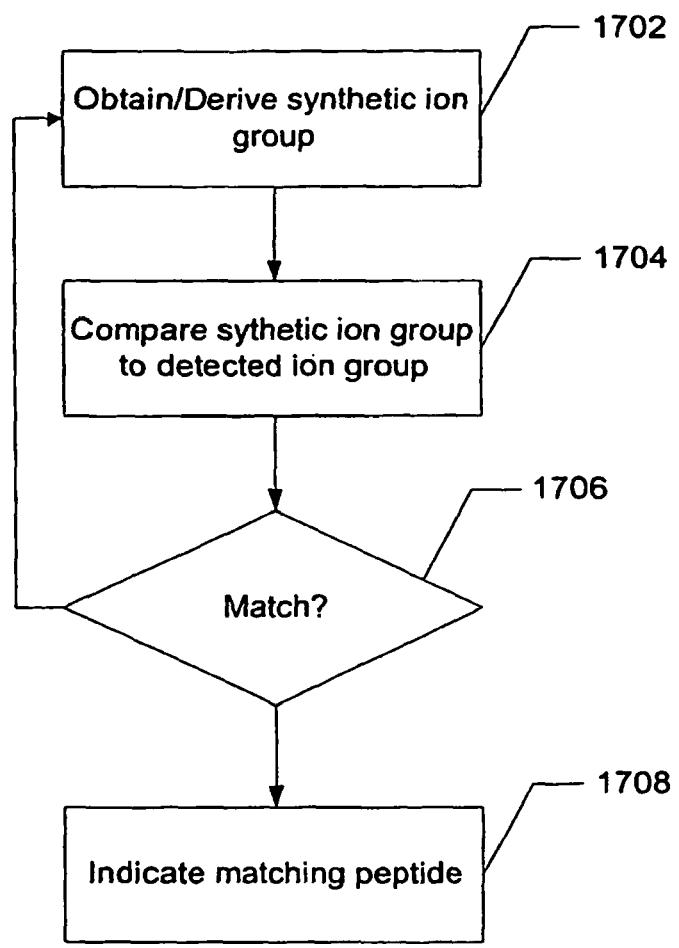
FIG. 17 is a flow chart for a method for identifying peptides using ion groupings identified using embodiments of the present invention.

The ion groupings identified using embodiments of the present invention can be used for a variety of purposes, which include peptide identification and identification of natural, synthetic, and semi-synthetic products. FIG. 17 is a flow chart for a method for identifying peptides using ion groupings identified using embodiments of the present invention. Once an ion group is determined according to an embodiment of the present invention, it is compared to a synthetic ion grouping obtained or derived from a database of protein sequences. Typically, the database of protein sequences is an indexed database of peptide sequences. The database can contain general protein sequences or be more focused and contain protein sequences directed to a particular biological entity or more likely to be seen in a particular study.

In step 1702*a* synthetic ion group is obtained from the database. The synthetic ion group can be pre-stored in the database or can be derived from peptide sequences stored in the database. To derive a synthetic ion group, a protein sequence in the database is digested in situ (artificially on a computer) using known cleavage sites to generate peptides. The peptides are then fragmented in situ into expected y- and b-ions. In step 1704 the y- and b-ions are compared to the ion group determined from embodiments of the present invention. If there is a match detected in step 1706, then in step 1708 that match is indicated as an identified peptide. If there is no match, then the process continues in step 1702 with another synthetic ion group obtained or derived from the database.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method of LC/MS analysis of a complex sample, comprising:
   collecting LC/MS data using multiple alternating cycles of high-energy and low-energy fragmentation within a time scale of a chromatographic peak to obtain spectra from high-energy fragment ions and low-energy precursor ions associated with an originating molecule of the complex sample, wherein each of the ions of the spectra has a chromatographic retention time and a peak profile; and grouping precursor ions and fragment ions that derive from a common originating molecule in response to a correspondence in the chromatographic retention times and one or more characteristics of the peak profiles of the precursor ions and fragment ions.

2. The method of claim 1, wherein the one or more characteristics of the peak profiles includes a peak shape symmetry.

3. The method of claim 1, wherein the one or more characteristics of the peak profiles includes an apex retention time.

4. The method of claim 1, wherein the one or more characteristics of the peak profiles includes a peak width.

5. The method of claim 1, wherein the one or more characteristics of the peak profiles includes a lift off time of initial detection.

6. The method of claim 1, wherein the one or more characteristics of the peak profiles includes a touch down time of final detection.

7. The method of claim 1, wherein the one or more characteristics of the peak profiles includes a normalized slope.

8. The method of claim 1, wherein the one or more characteristics of the peak profiles includes a time of an inflection point relative to a time of a peak apex denoting a maximum response.

9. The method of claim 1, wherein a TOF (time-of-flight)-based instrument is used in analyzing the complex sample to obtain the LC/MS data.

10. The method of claim 1, wherein said grouping forms a group of ions and excludes from the group any ion having a peak profile that is not similar to peak profiles of other ions in the group.

11. The method of claim 1, wherein said grouping forms a group of ions and includes ions in the group having a common chromatographic retention time and similar peak profiles.

12. The method of claim 11, wherein said grouping excludes from the group another ion having a retention time that is the common chromatographic retention time and a peak profile that is not similar to peak profiles of other ions in the group.

13. The method of claim 11, further comprising:
determining a second group of ions obtained or derived from a database;
comparing the group to the second group; and
determining, on the basis of said comparing, whether the group matches the second group of ions.

14. The method of claim 13, wherein the second group of ions identifies a molecule and, responsive to determining that the group matches the second group, the method includes identifying the molecule as being included in the complex sample.

15. The method of claim 14, wherein the second group of ions identifies a molecule that is any of a peptide, a metabolite, and a natural product.

16. A method of analyzing a complex sample, comprising:
receiving spectra obtained from analyzing the complex sample, said analyzing including using multiple alternating cycles of high-energy and low-energy fragmentation within a time scale of a chromatographic peak to obtain the spectra from high-energy fragment ions and low-energy precursor ions associated with an originating molecule of the complex sample, wherein each of the ions of the spectra has a chromatographic retention time and a peak shape; and grouping precursor ions and fragment ions that derive from a common originating molecule in response to a correspondence in the chromatographic retention times and one or more characteristics of the peak shapes of the precursor ions and fragment ions.

17. The method of claim 16, wherein the one or more characteristics of the peak shapes includes any one or more of peak shape symmetry, an apex retention time, a peak width, a lift off time of initial detection, a touch down time of final detection, a normalized slope, and a time of an inflection point relative to a time of a peak apex denoting a maximum response.

18. The method of claim 16, wherein a TOF (time-of-flight)-based instrument is used analyzing the complex sample to obtain the spectra.

19. The method of claim 16, wherein said grouping forms a group of ions and excludes from the group any ion having a peak shape that is not similar to peak shapes of other ions in the group.

20. The method of claim 16, wherein said grouping forms a group of ions and includes ions in the group having a common chromatographic retention time and similar peak shapes.

21. The method of claim 20, wherein said grouping excludes from the group another ion having a retention time that is the common chromatographic retention time and a peak shape that is not similar to peak shapes of other ions in the group.

22. A system comprising:
a processor; and
a memory including code stored therein that, when executed by the processor, performs processing that analyzes a complex sample, the processing comprising:
collecting LC/MS data using multiple alternating cycles of high-energy and low-energy fragmentation within a time scale of a chromatographic peak to obtain spectra from high-energy fragment ions and low-energy precursor ions associated with an originating molecule of the complex sample, wherein each of the ions of the spectra has a chromatographic retention time and a peak profile; and
grouping precursor ions and fragment ions that derive from a common originating molecule in response to a correspondence in the chromatographic retention times and one or more characteristics of the peak profiles of the precursor ions and fragment ions.

23. A system comprising:
a processor; and
a memory including code stored therein that, when executed by the processor, performs processing comprising:
receiving spectra obtained from analyzing the complex sample, said analyzing including using multiple alternating cycles of high-energy and low-energy fragmentation within a time scale of a chromatographic peak to obtain the spectra from high-energy fragment ions and low-energy precursor ions associated with an originating molecule of the complex sample, wherein each of the ions of the spectra has a chromatographic retention time and a peak shape; and grouping precursor ions and fragment ions that derive from a common originating molecule in response to a correspondence in the chromatographic retention times and one or more characteristics of the peak shapes of the precursor ions and fragment ions.

* * * * *